US010118721B2

(12) United States Patent
Niehr et al.

(10) Patent No.: US 10,118,721 B2
(45) Date of Patent: Nov. 6, 2018

(54) ROTARY FEED AND DEVICE FOR TREATING AND/OR FOR TRANSPORTING CONTAINERS, SAID DEVICE HAVING SUCH A ROTARY FEED

(71) Applicant: KHS GmbH, Dortmund (DE)

(72) Inventors: Thomas Niehr, Bad Münster am Stein Ebernburg (DE); Jürgen Franz Vorwerk, Mörsdorf (DE)

( * ) Notice: Subject to any disclaimer, the term of this patent is extended or adjusted under 35 U.S.C. 154(b) by 226 days.

(21) Appl. No.: 15/021,779

(22) PCT Filed: Aug. 7, 2014

(86) PCT No.: PCT/EP2014/067031

§ 371 (c)(1), (2) Date: Mar. 14, 2016

(87) PCT Pub. No.: WO2015/036186

PCT Pub. Date: Mar. 19, 2015

(65) Prior Publication Data

US 2016/0221701 A1 Aug. 4, 2016

(30) Foreign Application Priority Data

Sep. 12, 2013 (DE) ........................ 10 2013 110 016

(51) Int. Cl.

| | |
|---|---|
| ***A61L 9/00*** | (2006.01) |
| ***A61L 2/00*** | (2006.01) |
| ***F16K 11/00*** | (2006.01) |
| ***E03B 11/00*** | (2006.01) |
| ***B08B 3/00*** | (2006.01) |
| ***B65B 63/08*** | (2006.01) |
| ***B65B 55/10*** | (2006.01) |
| ***B67C 3/22*** | (2006.01) |

(52) U.S. Cl.
CPC ................ *B65B 55/10* (2013.01); *B67C 3/22* (2013.01); *B67C 2003/228* (2013.01)

(58) Field of Classification Search
CPC .... B67C 3/00; B67C 3/22; B67C 3/28; B65B 55/02; F16C 33/72; A61L 2/0088; A61L 2/0094
USPC ............. 422/28, 32, 34, 292, 300, 305, 307; 137/238, 341, 577; 134/103.2, 105; 53/127, 266.1, 111 R
See application file for complete search history.

(56) References Cited

U.S. PATENT DOCUMENTS

| | | | | |
|---|---|---|---|---|
| 6,918,417 B2 * | 7/2005 | Bernhard | ................ | B67C 3/244 141/148 |
| 2012/0018030 A1 * | 1/2012 | Laumer | ................... | B67C 3/001 141/1 |
| 2012/0174529 A1 | 7/2012 | Clüsserath | | |

FOREIGN PATENT DOCUMENTS

| | | |
|---|---|---|
| CN | 101432209 | 5/2009 |
| CN | 101448728 | 6/2009 |

(Continued)

*Primary Examiner* — Monzer R Chorbaji

(57) ABSTRACT

A rotary feed includes a static part that remains stationary relative to a stationary reference frame and a rotating part that rotates with a rotor. The static part and rotating part run adjacent to each other and define a sealed flow channel for a first medium. A buffer chamber surrounds the static and rotating parts, and the transition between these parts. During operation, a barrier medium charges it at a transition between the static and rotating parts. An outlet connects the buffer chamber to a treatment head to permit a medium in the buffer to be fed to the nozzle for container treatment.

13 Claims, 9 Drawing Sheets

(56) References Cited

FOREIGN PATENT DOCUMENTS

| | | | | |
|---|---|---|---|---|
| CN | 101848775 | | 9/2010 | |
| DE | 10 2007 060 392 | | 6/2009 | |
| DE | 10 2008 017768 | | 10/2009 | |
| EP | 2030941 | | 3/2009 | |
| EP | 2455325 | | 5/2012 | |
| JP | H09 12013 | | 1/1997 | |
| WO | 2008/019831 | | 2/2008 | |
| WO | WO 2008/019831 | A1 * | 2/2008 | ............... F16J 15/00 |

* cited by examiner

ROTARY FEED AND DEVICE FOR TREATING AND/OR FOR TRANSPORTING CONTAINERS, SAID DEVICE HAVING SUCH A ROTARY FEED

RELATED APPLICATIONS

This is the national stage entry under 35 USC 371 of international application PCT/EP2014/067031, filed on Aug. 7, 2014, which claims the Sep. 12, 2013 priority date of German application DE 102013110016.3, the contents of which are herein incorporated by reference.

FIELD OF INVENTION

The invention relates to container processing, and in particular, to coupling media from a stationary reference frame to a rotating reference frame.

BACKGROUND

Known container-treatment devices include rotating machines with processing positions on a periphery thereof. In these machines, container treatment involves applying treatment medium while the containers are moving. This requires some kind of rotary joint to bring treatment media from a stationary reference frame into a rotating reference frame.

A typical rotary joint has one stationary part and one rotating part. There are also flow channels for both media. These are sealed from each other and from the exterior by mechanical seals that extend through both parts of the rotary joint.

To suppress entry of bacteria or other contaminants into these flow paths, it is usual to provide barrier spaces between the joint's two parts and to fill these barrier spaces with a barrier medium that differs from the treatment medium. The barrier medium is often a hot vapor.

The need to use a barrier medium is a disadvantage. First, it is one more consumable to supply and pay for. Second, it creates the need for a complex design that prone to failure. Additionally, its pressure must be monitored constantly to detect leakage.

To make matters worse, the barrier medium is usually heated. This heat stresses the various seals, thus reducing their service life.

SUMMARY

An object of the invention is to provide a rotary feed that avoids the aforesaid.

The rotary feed is typically part of a complete system for the sterile and/or aseptic filling of products into containers. The rotary feed has a rotary part that rotates with a transport element and a static part that does not move, and is arranged on a machine frame of the device or on part of a housing of the system for aseptic and/or sterile filling. The rotating part is provided on the transport element or on a rotating rotary feed part of the transport element in such a way that the axis of rotation of the rotary feed is on the same axis as the axis of rotation of the transport element.

The rotary feed forms at least two separate flow paths for two different treatment media. One path can be used for a liquid sterilization medium, while the other path can be used for a sterile medium.

One flow path is formed by an outer annular chamber that is configured partly on the non-moving rotary feed part and partly on the rotating rotary feed part of the rotary feed. Liquid sterilization medium flows through this flow path, which is connected to the treatment heads and/or nozzles on the rotating transport element. At least one further flow path is formed by flow channels that run adjacent to one another in the non-moving and in the rotating rotary feed part. An outer annular chamber surrounds the two rotary feed parts over at least a partial length of a face or side lying outside their axis of rotation, and also surrounds the transition between the two rotary feed parts, at the same time forming a buffer space which prevents the penetration of bacteria and/or contaminants. This obviates the need for additional vapor barriers and buffer chambers or spaces that having complex seals and that have to be charged with an additional barrier medium.

Whether under pressure or not, the other sterile medium can be fed as a gaseous and/or vaporous medium or as a liquid medium through the rotary feed.

An advantage of the foregoing rotary feed is the absence of any separate barrier medium and the elimination of any need to monitor a barrier medium. Another advantage is its cost-effective layout. This arises, for example, from a reduction in the required number of sealing points, which in turn reduces maintenance effort and maintenance costs, and leads to a considerable increase in service life.

In one aspect, the invention features an apparatus for use in container treatment. Such an apparatus includes a rotary feed for supplying first and second media from a stationary reference frame to nozzles being moved by a rotor around an axis of rotation. The rotary feed includes a static part that remains stationary relative to the stationary reference frame and a rotating part that rotates with the rotor. The static part and rotating part run adjacent to each other and define a sealed flow channel for a first medium. A buffer chamber surrounds the static and rotating parts, and the transition between these parts. During operation, it is charged with a barrier medium at a transition between the static and rotating parts. An outlet connects the buffer chamber to a treatment head to permit a medium in the buffer to be fed to the nozzle for container treatment.

In some embodiments, a portion of the static part surrounds a portion of the rotary part. However, in other embodiments, the configuration is the other way around. In these embodiments, a portion of the rotary part surrounds a portion of the static part.

Other embodiments include a first part coupled to the rotating part and a second part coupled to the static part. Each of these parts has an opening therethrough. The first and second cooperate to define the buffer chamber.

Additional embodiments are those in which the static part includes a first tube and the rotating part includes a second tube. In these embodiments, at least a portion of the first tube is adjacent to at least a portion of the second tube.

Other embodiments are those that have a guide way and a guide ring that define a plain bearing.

In yet other embodiments, the liquid sterilization medium is a liquid that releases gaseous bactericidal constituents.

Also among the embodiments of the invention are those that have an annular chamber that extends radially from a surface of the rotary part to a surface of the static part and that extends axially from a first ring seal and a second ring seal. These embodiments include an inter-chamber opening that connects the buffer chamber and the annular chamber.

Some embodiments include a fill-level sensor disposed to measure a liquid level in the buffer chamber.

Yet other embodiments include an annular chamber that receives liquid sterilization medium from the buffer chamber.

Other embodiments include a heater in the buffer chamber for promoting excitation of the liquid sterilization medium within the buffer chamber. This excitation promotes the release of bactericidal constituents from the liquid sterilization medium.

Yet other embodiments also include a rotor having treatment positions on a periphery thereof. The rotor is driven to rotate about a machine axis. Each of the treatment positions has a treatment head that switches between delivering a sterile medium and delivering a sterile medium that has been mixed with an atomized spray of liquid sterilization medium.

In another aspect, the invention features a method for delivering media to a treatment head for treating containers. Such a method placing a container into a treatment station on a periphery of a rotor that rotates relative to a stationary reference frame, passing the first and second media into a rotary feed that includes a rotating part that moves with the rotor and a static part that remains stationary relative to the stationary reference frame, and conveying the media to the treatment head. Passing the first medium includes passing it into a flow channel formed by the static and rotating parts. In contrast, passing the second medium includes passing it into a buffer chamber that surrounds the static part and the rotating part.

As used herein, "containers" cans, bottles, tubes, and pouches, whether made from metal, glass and/or plastic, and other packaging media, in particular including packages that are suitable for filling products that are in powdered form, granular form, and in the form of viscous or pasty liquids.

As used herein, terms such as "essentially", "in essence" or "around" refer to variations from an exact values by ±10%, preferably by ±5%, and/or variations in the form of changes that are insignificant for function.

Further embodiments, advantages, and possible applications of the invention arise out of the following description of embodiments and out of the figures. All of the described and/or pictorially represented attributes whether alone or in any desired combination are fundamentally the subject matter of the invention independently of their synopsis in the claims or a retroactive application thereof. The content of the claims is also made an integral part of the description.

The invention is explained in detail below through the use of embodiment examples with reference to the figures, in which:

DETAILED DESCRIPTION

Figure 1:
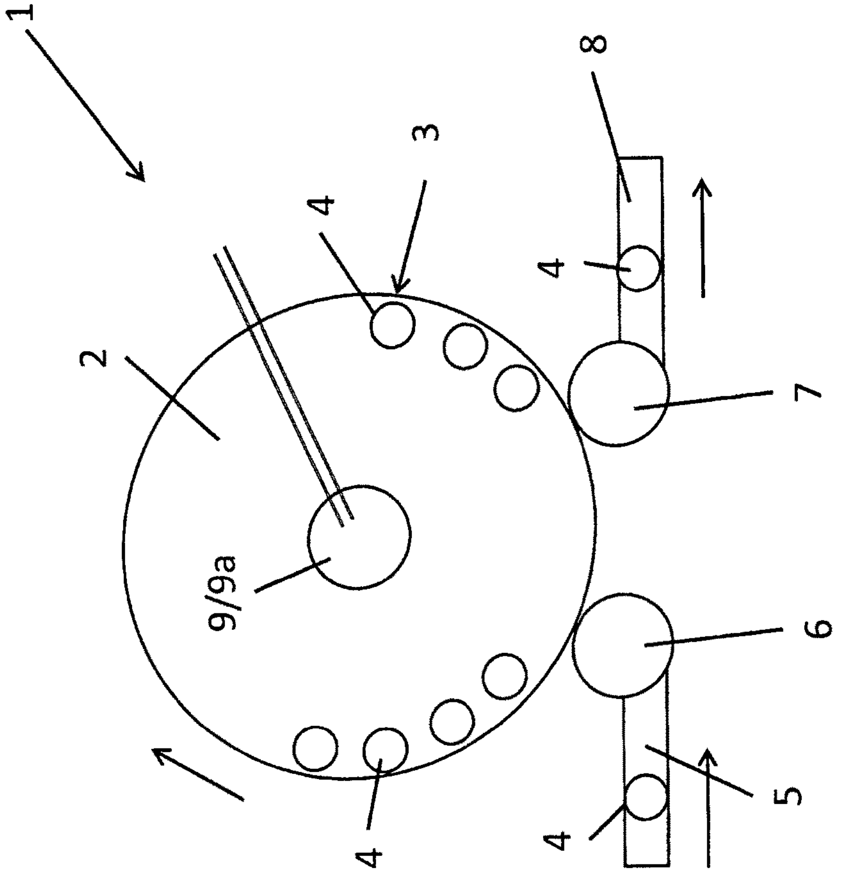
FIG. 1 shows a top view of a machine for transporting and treating containers.
Figure 2:
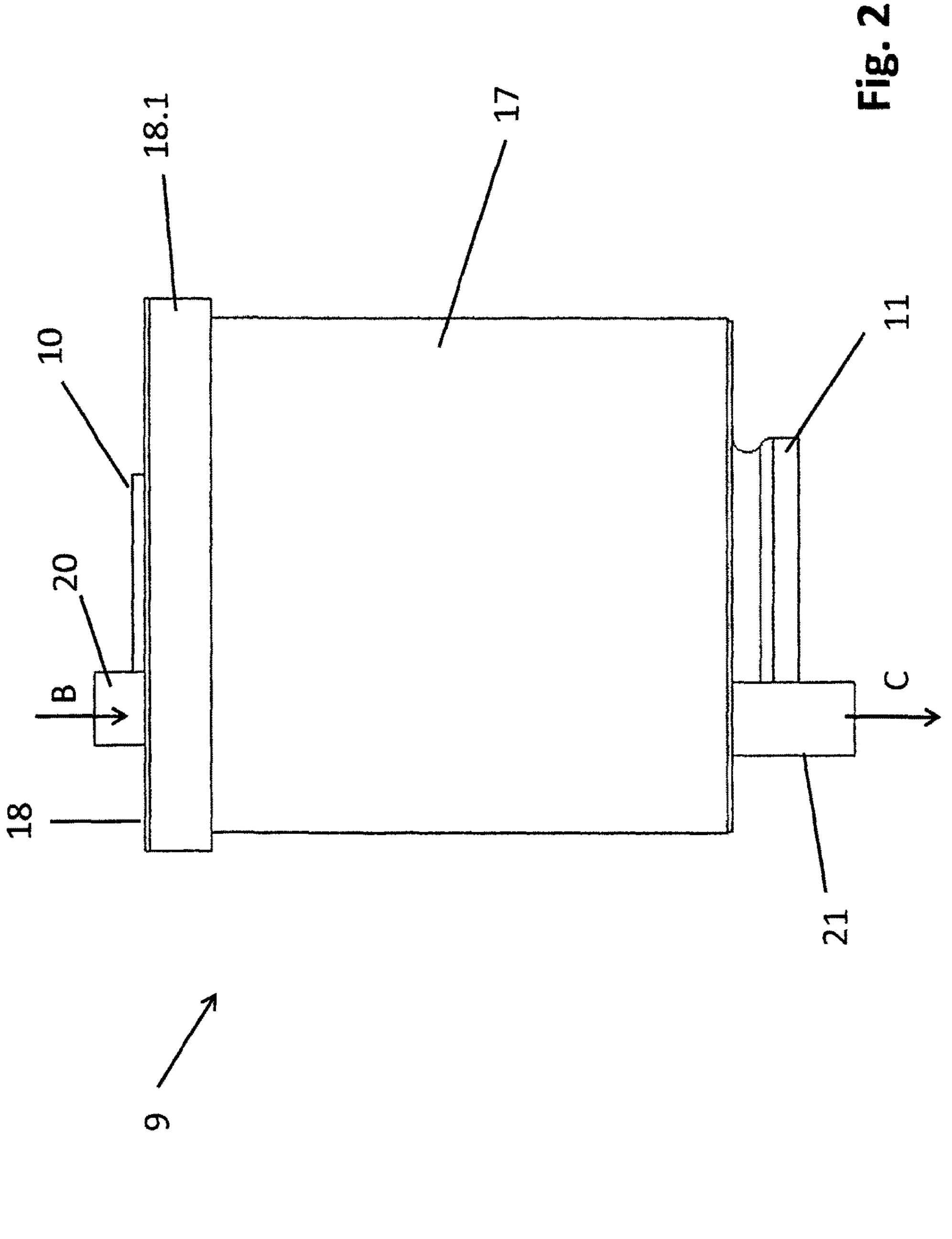
FIG. 2 shows a side view of a rotary feed for two media for use with the container treatment machine of FIG. 1.

FIG. 1 shows a rotary container-treatment machine 1 having a rotor 2 that rotates about a vertical machine-axis. Around the periphery of the rotor 2 are treatment positions 3 for treating containers 4. The container-treatment machine 1 cleans, disinfects and/or sterilizes containers 4 with liquid sterilization-medium. An example of such a medium is a concentrated aqueous solution of hydrogen peroxide. A rotary container-treatment machine 1 such as that shown in FIG. 1 is typically part of a facility that carries out aseptic filling of containers 4 with liquid filling material.

Nozzles at the treatment positions 3 apply hot sterilization medium to the inner surfaces of containers 4. This medium can be liquid or gas. After the containers 4 have been sufficiently sterilized by the medium, nozzles sterile gas into the container 4.

A first outer transporter 5 passes containers 4 that are to be treated to a container inlet 6, which loads them into treatment positions 3. After having been treated, a container outlet 7 unloads the containers 4 and places them on a second outer transporter 8, which then takes them away.

A supply unit supplies various media to the rotor 2 and, ultimately, to the nozzles and/or treatment heads provided at the various treatment positions 3. It does so through a rotary feed 9, as shown in FIGS. 1-4.

Figure 3:
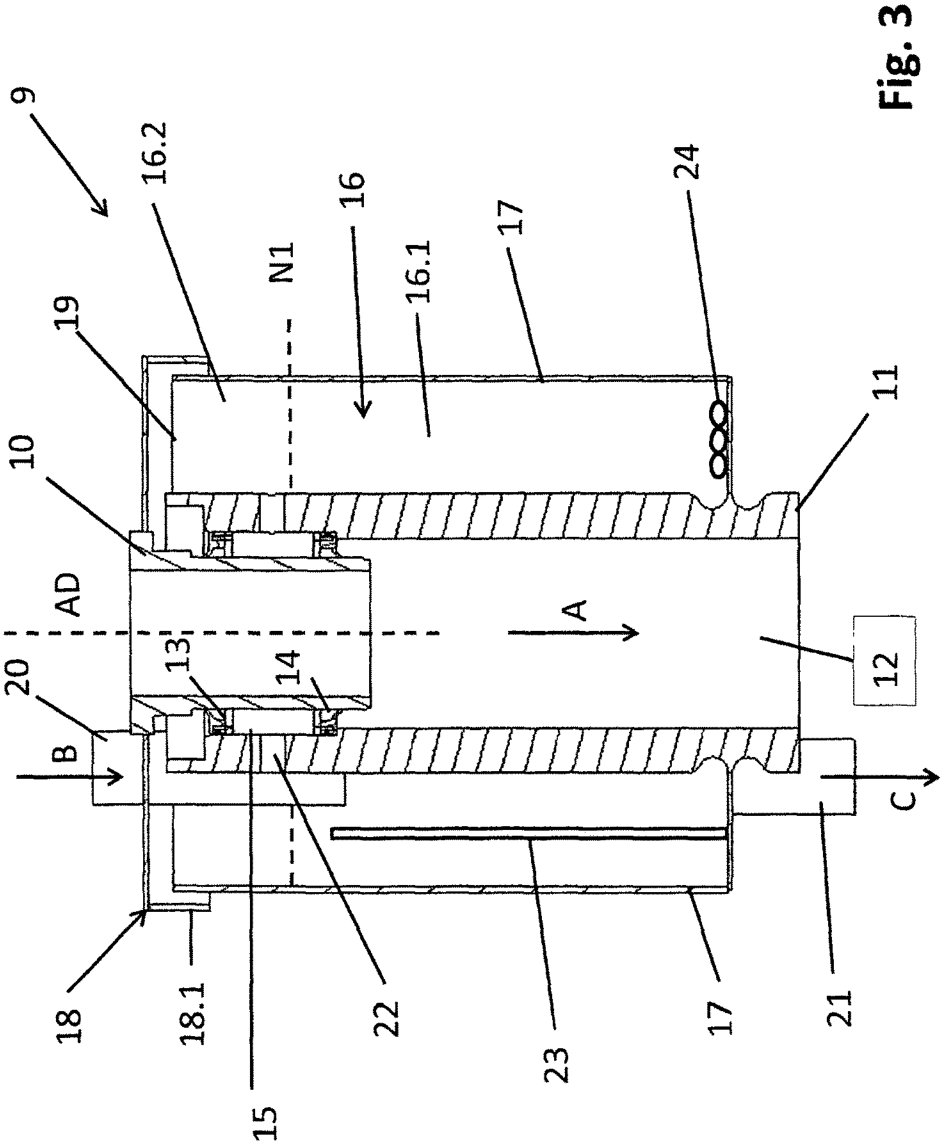
FIG. 3 shows a cross-section through a rotary feed of FIG. 2.
Figure 4:
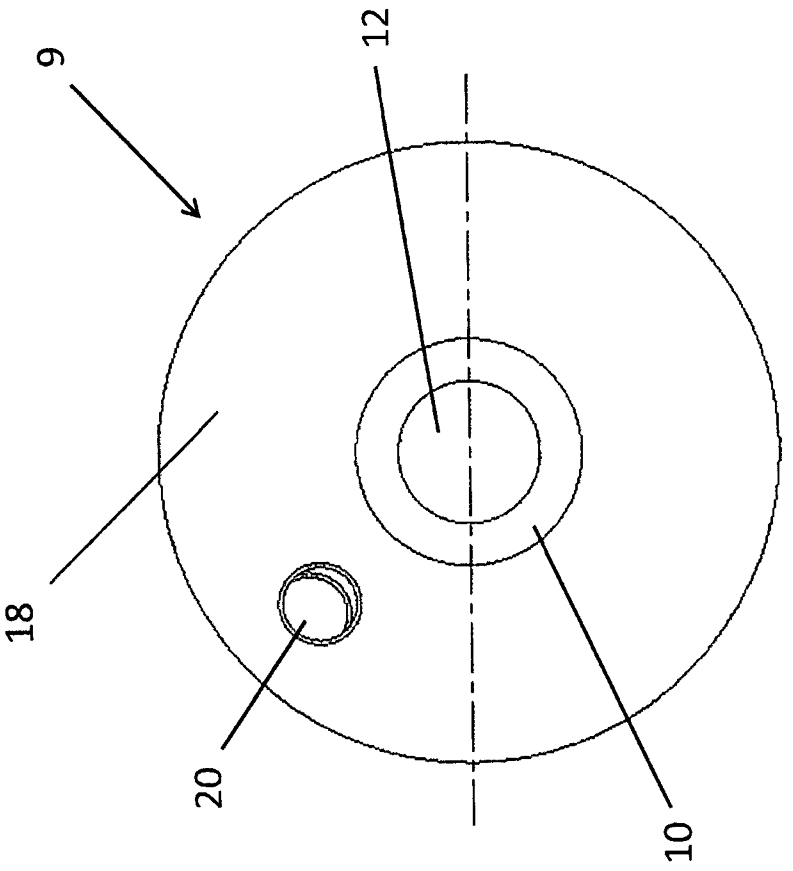
FIG. 4 shows the rotary feed of FIG. 2 in plan view.

Referring now to FIG. 3, the rotary feed 9 extends along a feed axis AD that is coincident with the machine axis. It includes a static part 10 and a rotating part 11. As shown in FIG. 3, the rotating part 11 encloses part of the static part 10.

The rotating part 11 connects to the rotor 2. As such, it rotates about the feed axis AD. Meanwhile, a portion of the static part 10 protrudes out of the rotating part 11 and connects to a machine part that does not rotate with the rotor 2.

The static and rotating parts 10, 11 form a continuous inner channel 12 that guides sterile medium along a first flow direction A from an external supply towards the treatment positions 3. First and second ring seals 13, 14 between the static and rotating parts 10, 11 seal off the inner channel 12. The first and second ring seals 13, 14 lie against a cylindrical outer face of the static part 10 and against a cylindrical inner surface of the rotating part 11. A gap extending along the feed axis AD separates the first and second ring seals 13, 14. This gap defines an annular chamber 15 bounded by the first and second ring seals 13, 14 and the walls of the static and rotating parts 10, 11.

A housing 17 on the rotating part 11 and a cover 18 of the static part 10 define a buffer chamber 16 that surrounds the outsides of the static and rotating parts 10, 11. A plurality of inter-chamber openings 22 connects the annular chamber 15 to the buffer chamber 16. An annular opening 19 at the top of the housing provides an opening into the housing's interior, which is otherwise closed off at its base and sides. The annular opening 19 is at or slightly above the upper end of the rotating part 11.

The static part's cover 18 covers the annular opening 19. The cover 18 has a rim 18.1 that concentrically surrounds the feed axis AD. The rim 18.1 angles downwards to overlap an edge of the annular opening 19. Because the cover 18 is at a distance from the housing 17, it avoids impeding the rotating part 11 as it turns with the housing 17 about the feed axis AD.

A tube section forms a first-medium inlet 20 that reaches into the buffer chamber 16. During operation, liquid sterilization medium passes through the first-medium inlet 20 along a first medium feed direction B. Meanwhile, a first-medium outlet 21 at the housing's base discharges the liquid sterilization medium from the buffer chamber 16 along a discharge direction C. This discharged liquid sterilization-medium is eventually fed to the nozzles or treatment heads at the treatment positions 3.

The liquid sterilization-medium divides the buffer chamber 16 into a lower liquid space 16.1 below the fill-level N1 and a head space 16.2 above the fill-level N1. During operation, the liquid sterilization-medium releases various gaseous constituents that collect in the head space 16.2. When the liquid sterilization-medium is hydrogen peroxide, these gaseous constituents include radical oxygen atoms. An electric heater 24 in the buffer chamber 16 applies energy to the liquid sterilization medium to assist in releasing the medium's bactericidal constituents.

A filling-level sensor 23 assists in controlling the feeding and discharge of liquid sterilization medium in an effort to maintain a constant fill-level N1 of medium in the buffer chamber 16. In some embodiments, the filling-level sensor 23 is an inductive filling-level sensor. Preferably, the fill-level N1 is set so it is below the inter-chamber openings 22. This allows the gaseous bactericidal constituents of the sterilization medium also enter the annular chamber 15 through the inter-chamber openings 22 but avoids having the liquid sterilization medium itself pour through the inter-chamber openings 22 into the annular chamber 15.

As FIG. 3 also specifically shows, the buffer chamber 16 encloses the outer surfaces of the static and rotating parts 10, 11 as well as the transition between the static and rotating parts 10, 11. The outer surfaces are those surfaces that face away from the feed axis AD.

FIGS. 5-8 show a rotary feed 9*a* that includes a static part 10 and a rotary feed part 11. The static part 10 does not rotate with the transport element or rotor 2. The rotary feed part 11 connects to the rotating transport element or rotor 2 and rotates about the feed axis AD.

In this embodiment, static and rotating tubes 25, 26 form the static and rotating parts 10, 11 respectively.

Figure 5:
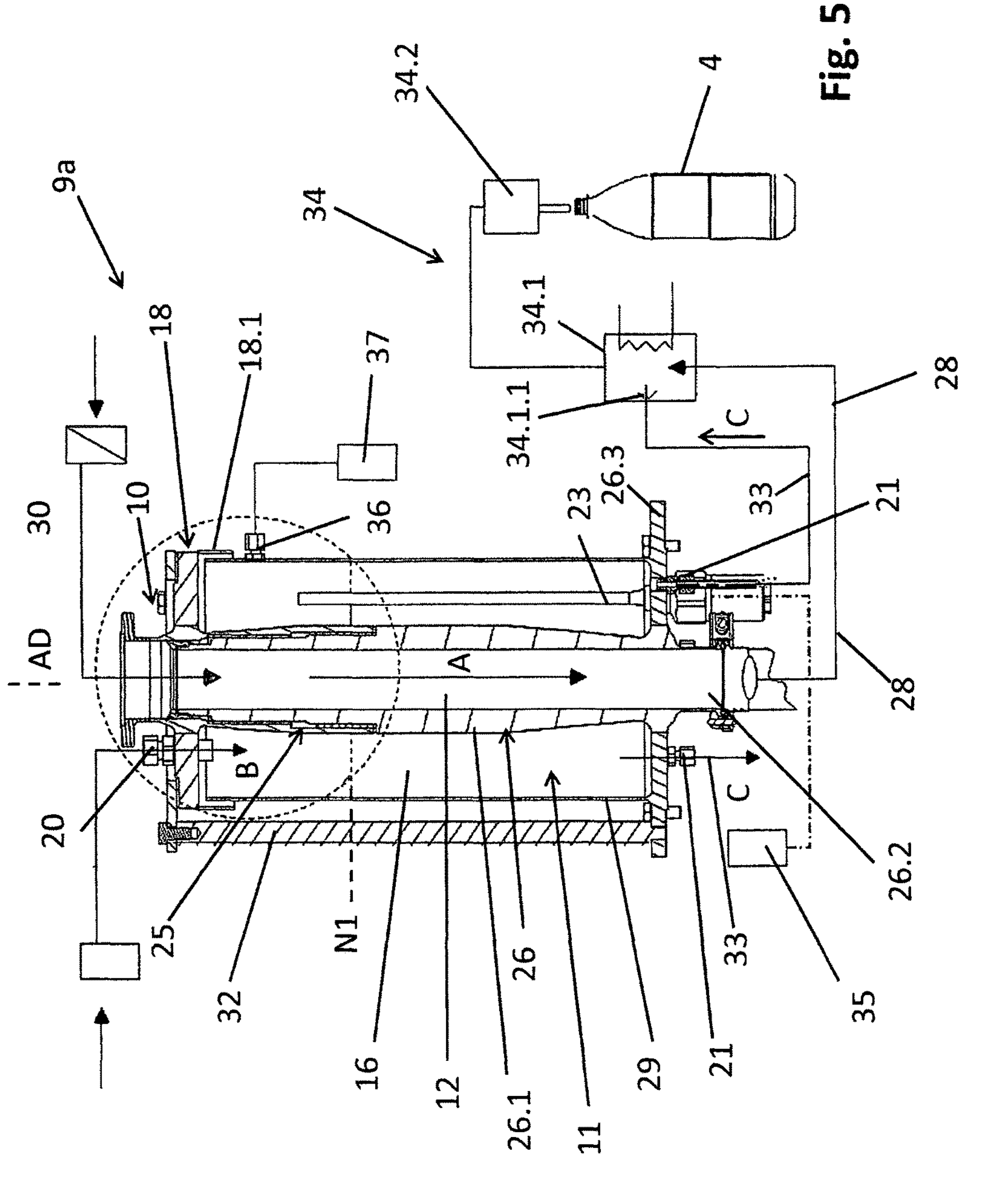
FIG. 5 shows a section through a further embodiment of the rotary feed, together with a container-treatment station.
Figure 6:
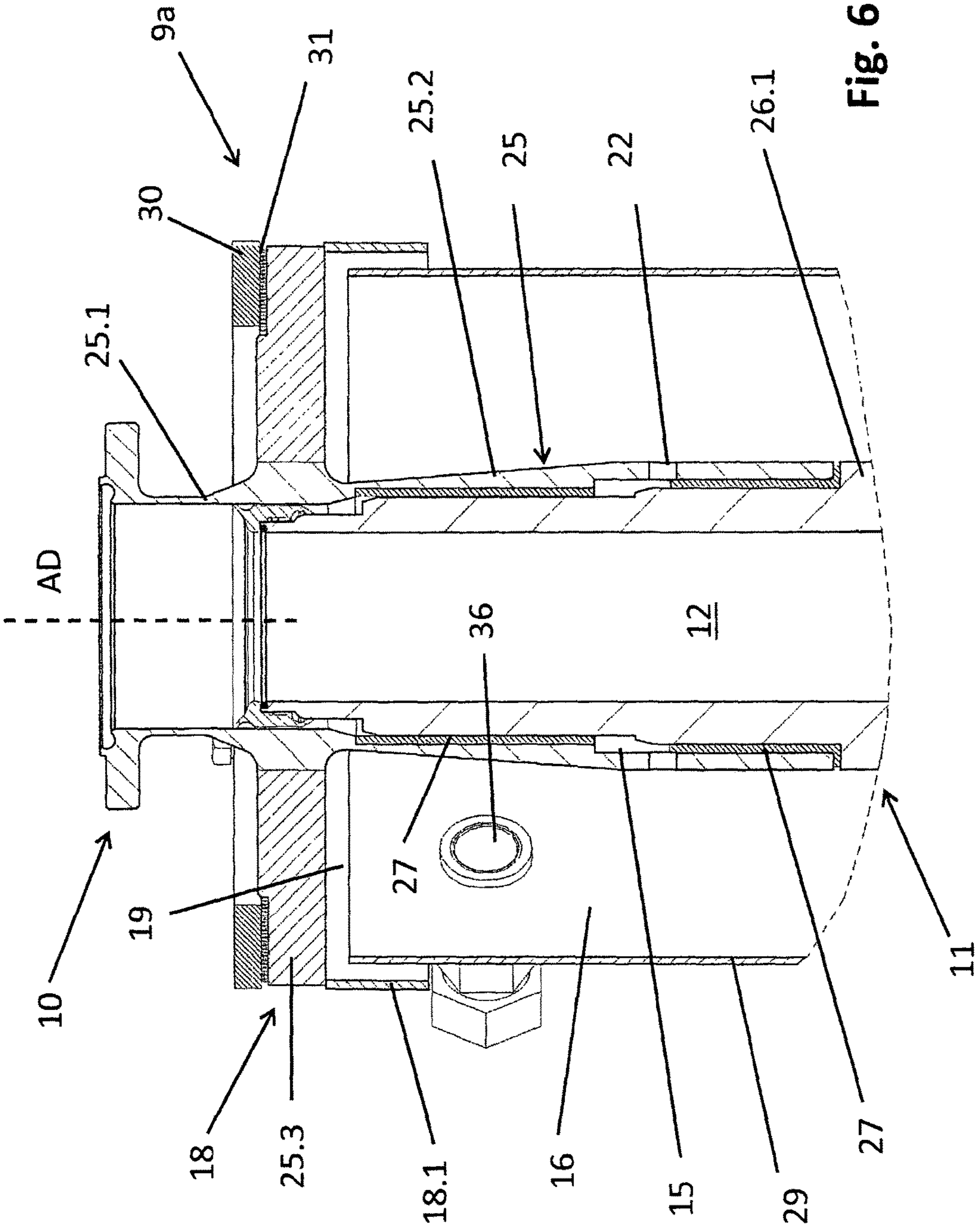
FIGS. 6 and 7 show details of the rotary feed of FIG. 3.
Figure 7:
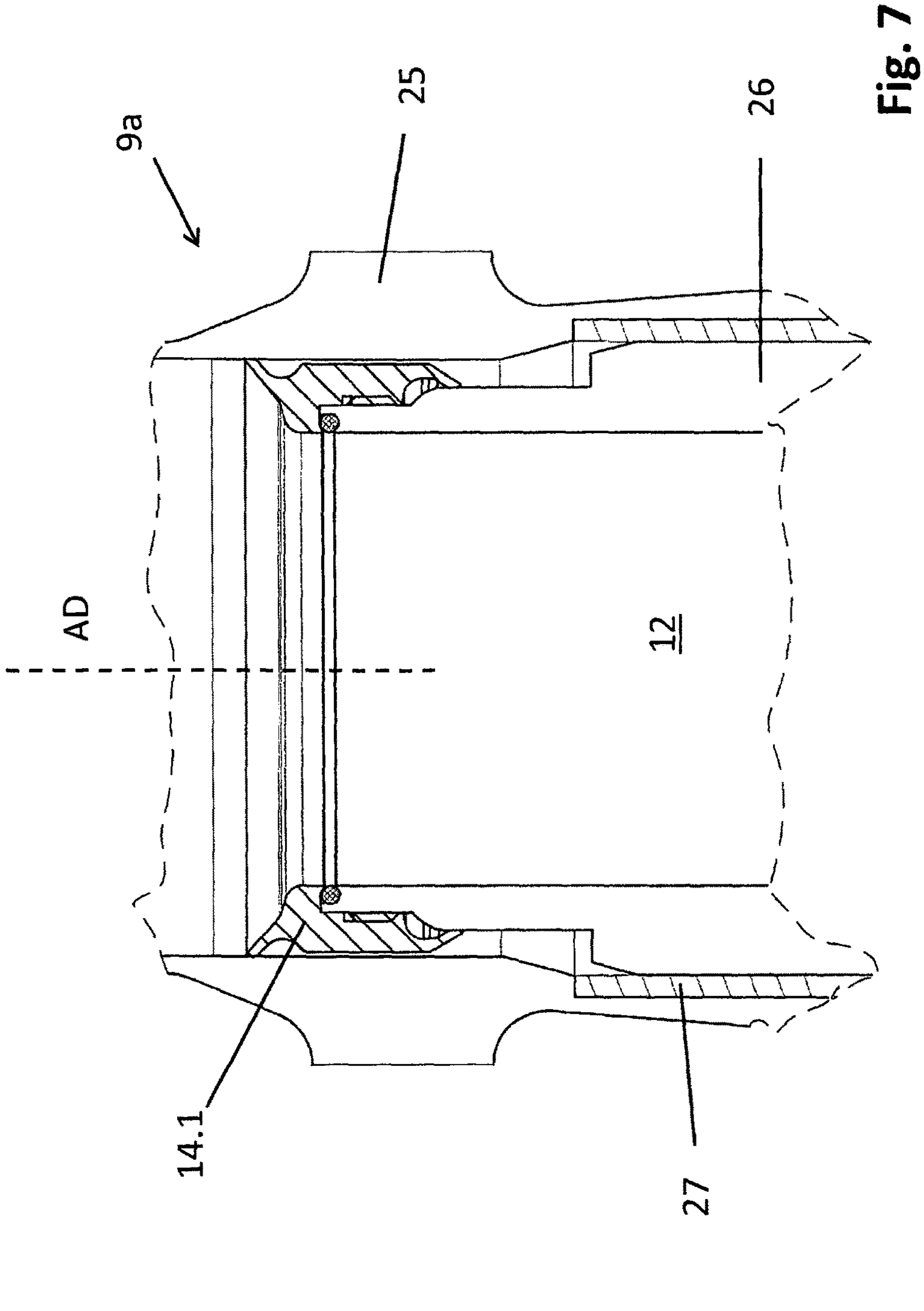
Figure 8:
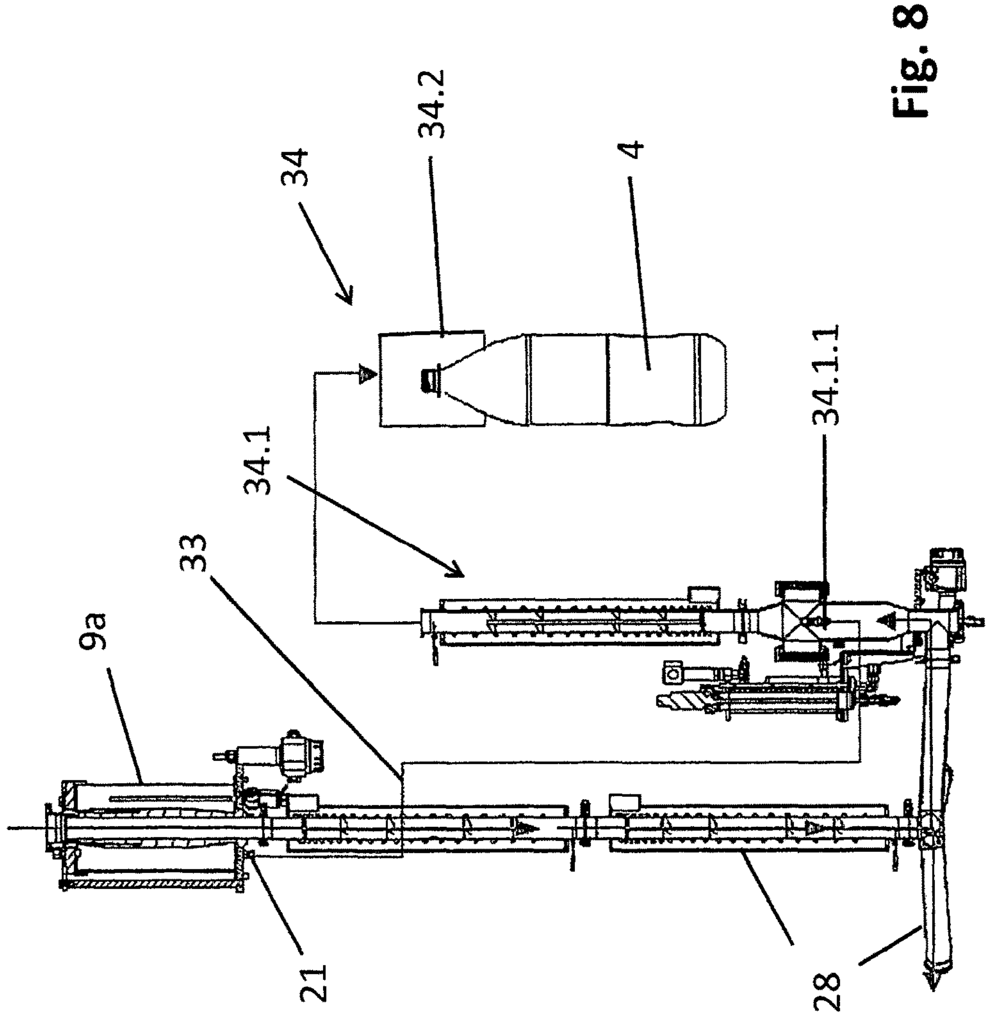
FIG. 8 shows the rotary feed of FIG. 5, together with a pipe system or connection system for feeding the further sterile medium to a container-treatment position.

Referring to FIG. 6, the static tube 25 has an uppermost section that defines a mating flange 25 and a surrounding section 25.2. Between the mating flange 25.1 and the surrounding section 25.2 is an intermediate section. The rotating tube has a surrounded section 26.1 and an free section 26.2, the latter being best seen in FIG. 5.

The mating flange 25.1 protrudes away from rotary feed 9*a* and connects to a static line carrying sterile medium. The intermediate section engages a cover ring 25.3. The surrounding section 25.2 encloses the surrounded section 26.1 of the rotating tube 26.

Axially offset bearings 27 fill a gap between an outer surface of the surrounded section 26.1 and an inner surface of the surrounding section 25.2. These bearings 27 fulfill a function similar to that of the first and second ring seals 13, 14 shown in FIG. 3.

Between the two bearings 27 is an annular chamber 15, best seen in FIG. 6. The inter-chamber openings 22 connect the annular chamber 15 to a buffer chamber 16 are also provided in surrounding section 25.2. As well as bearing elements 27, a ring seal 14.1 is provided at the upper end of surrounded section 26.1 between the outer face of element 26 and the inner face of the static tube 25.

The cover ring 25.3 occupies a space that extends radially outward from the intermediate portion of the static tube 25. The cover ring's upper and lower sides are coplanar with planes that are perpendicular to the feed axis AD. The cover ring 25.3 forms a cover 18 having a ring-shaped cover flange 18.1 that protrudes downwards from the underside of the cover ring 25.3.

The free section 26.2 of the rotating tube 26 protrudes beyond the underside of the rotary feed 9*a*, as shown in FIG. 5. A base ring 26.3 extends radially outward from the rotating tube 26 and defines a flange having upper and lower sides that are square to the feed axis AD. The upper side of the base ring 26.3 faces the static tube 25 and the lower side of the base ring 26.3 faces away from the static tube 25. An inner peripheral surface of the base ring 26.3 contacts the rotating tube 26 between the surrounded section 26.1 and the free section 26.2.

The base ring 26.3 thus forms the closed base of the buffer chamber 16. A cylindrical wall 29 encircling the rotating tube 29 forms the closed side of the buffer chamber 16. The cylindrical wall 29 is spaced apart from the rotating tube 26 and coaxial with the rotating tube 26. Together, the cylindrical wall 29 and the base ring 26.3 form a housing 17.

Referring back to FIG. 6, a guide ring 30 on the upper side of the cover ring 25.3 axially secures the connection between the static and rotating tubes 25, 26. The guide ring 30 lies against a guide way 31 located at a peripheral portion of the cover ring's upper side. Both the guide ring 30 and the guide way 31 are concentric with and surround the feed axis AD. The guide ring 30 and the guide way 31 define a plain bearing that permits relative rotation of the static and rotating parts 10, 11.

Referring now to FIG. 5, a plurality of rods 32 extends parallel to the feed axis AD. These rods 32 connect the guide ring 30 to the base ring 32 at points radially outside the cover 18 and the cover flange 18.1. As a result of these rods 32, the static and rotating parts 10, 11 are axially secured to one another so that they cannot move relative to each other in the axial direction.

The guide ring 30 encloses a region of the cover 18 through which a first-medium inlet 20 passes. This first-medium inlet 20 feeds liquid sterilization medium into the buffer chamber 16 along a first medium feed direction.

A plurality of first-medium outlets 21 pass through the base ring 26.3. These first-medium outlets 21 are circumferentially disposed around the feed axis AD. A line 33 connects to each first-medium outlet 21 to liquid sterilization medium to a treatment head 34 along a discharge direction C.

A fill-level sensor 23 within the buffer chamber 16 provides an output signal to a controller 35 that maintains a constant level N1 in the buffer chamber 16 by controlling the supply of the liquid sterilization medium entering the buffer chamber 16 through the first-medium inlet. An overflow opening 36 formed on the wall 29 above the level N1 connects to an overflow chamber 37 on the rotating transport element in case the controller 35 fails to control the level N1 correctly.

The first and second tubes 25, 26 form an inner channel 12 that passes through the rotary feed 9*a* and that is sealed off from the exterior. This inner channel 12 can carry sterile gas to the treatment heads 34 via a distribution system 28 connected to the free end 26.2.

A typical treatment head 34 includes a heater 34.1 through which the other sterile medium, such as sterile air, flows. This heater 34.1 heats the sterile medium. An atomizer nozzle 34.1.1 brings a fine spray of atomized liquid-sterilization medium for mixing with the sterile medium.

In the application phase, a nozzle 34.2 introduces the mixture of sterile air and atomized liquid-sterilization into a container 4. The nozzle 34.2 preferably includes a spray tube that enters the container's interior during treatment. In a subsequent treatment phase, the supply of the mixture liquid sterilization medium to nozzle 34.1.1 is interrupted so that only heated sterile medium enters the container 4.

Figure 9:
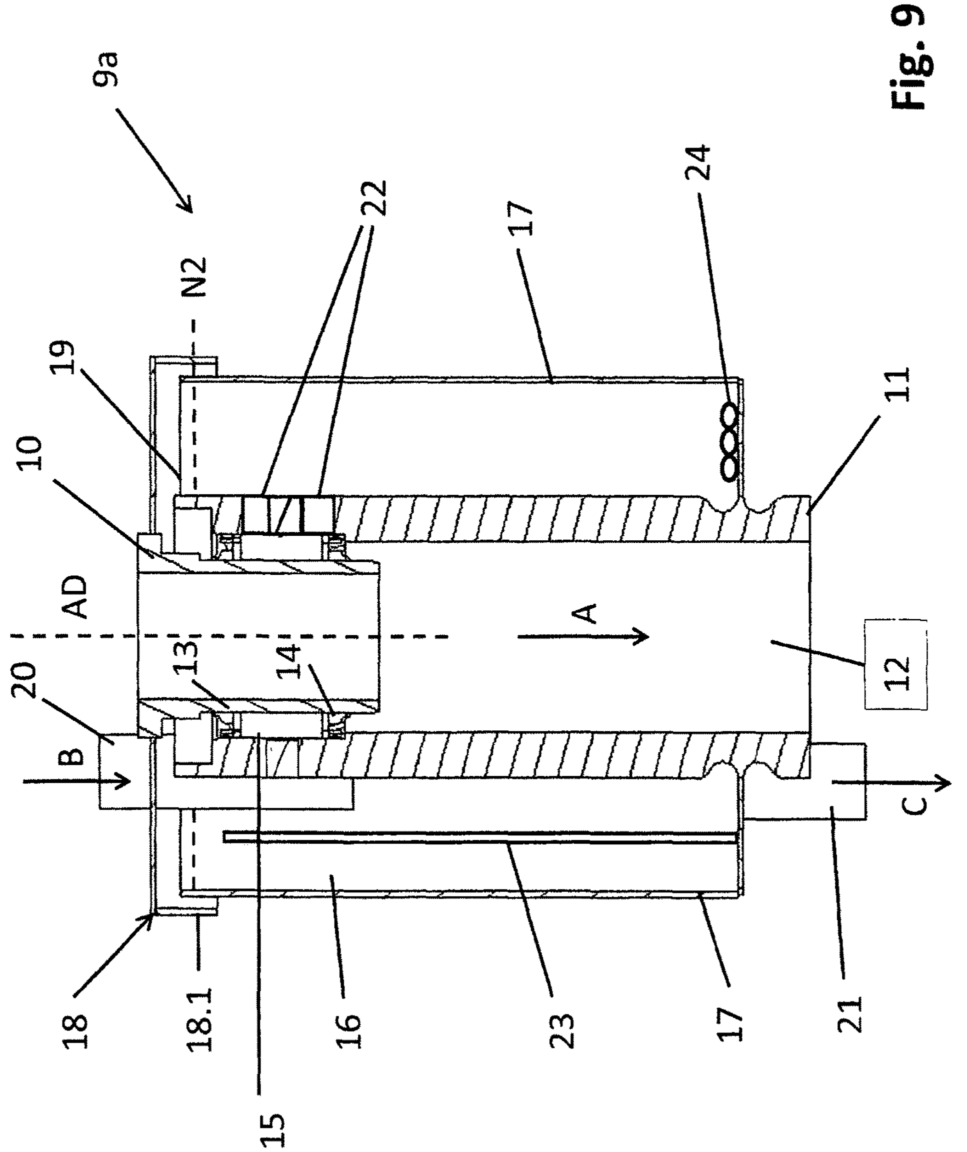
FIG. 9 shows a representation similar to FIG. 3 for a further embodiment.

FIG. 9 shows a rotary feed 9*b* that is similar to that shown in FIG. 3 with the exception that its inter-chamber openings 22 are provided in two groups that are axially offset from one another relative to feed axis AD. In this embodiment, the e level of the liquid sterilization medium in the buffer chamber 16 is maintained at fill-level N2 that is above all of the inter-chamber openings 22. This allows the annular chamber 15 to be flooded with the liquid sterilization medium.

A particular advantage of the rotary feeds described herein is the realization of a particularly simple and reliable barrier to penetration by outside contaminants into the inner channel 12 through the liquid sterilization medium flowing through the buffer chamber 16 and, in particular, through the bactericidal constituents released by this sterilization medium, which can escape through a gap formed between cover 18 and housing 17, and the use of liquid sterilization medium both for actual treatment and as a barrier medium. This avoids the need to supply a separate barrier medium.

The apparatus as described herein permits execution of a method that, immediately before the filling of the containers and not merely during a CIP operation, passes sterilization medium from a storage tank or supply pipe in only one path into the inner spaces of a central rotary feed and then passes it on for use in aseptic surface treatment of the transported containers 4.

The invention has been described hereinbefore by reference to embodiments. It goes without saying that numerous variations as well as modifications are possible without departing from the inventive concept underlying the invention.

Having described the invention, and a preferred embodiment thereof, what we claim as new, and secured by letters patent is:

1. An apparatus for use in container treatment, said apparatus comprising a rotary feed for supplying first and second media from a stationary reference frame to nozzles that are being moved by a rotor around an axis of rotation, said rotary feed comprising a static part, a rotating part, and a buffer chamber, wherein, during operation, said rotating part rotates with said rotor, said static part remains stationary relative to said stationary reference frame, and a barrier medium charges said buffer chamber at a transition between said static and rotating parts, wherein said static part and said rotating part run adjacent to one another, wherein said static part and said rotating part define a flow channel for a first medium, wherein said flow channel is sealed, wherein said buffer chamber at least partially surrounds said static and rotating parts, wherein said buffer chamber surrounds said transition between said static and rotating parts, and wherein an outlet connects said buffer chamber to a treatment head to permit a medium in said buffer to be fed to said nozzle for container treatment.

2. The apparatus of claim 1, wherein a portion of said static part surrounds a portion of said rotary part.

3. The apparatus of claim 1, wherein a portion of said rotary part surrounds a portion of said static part.

4. The apparatus of claim 1, further comprising a first part, a second part, a first opening, and a second opening, wherein said first part is coupled to said rotating part and said second part is coupled to said static part, wherein said first opening is an opening through said first part, wherein said second opening is an opening through said second part, wherein said first part and said second part cooperate to define said buffer chamber.

5. The apparatus of claim 1, wherein said static part comprises a first tube and said rotating part comprises a second tube, wherein at least a portion of said first tube is adjacent to at least a portion of said second tube.

6. The apparatus of claim 1, further comprising a guide way and a guide ring that define a plain bearing.

7. The apparatus of claim 1, wherein walls defining said buffer chamber are structurally configured to accommodate a liquid sterilization medium that releases gaseous bactericidal constituents.

8. The apparatus of claim 1, further comprising an annular chamber, a first ring seal, a second ring seal, and an inter-chamber opening that connects said buffer chamber and said annular chamber, wherein said annular chamber extends radially from a surface of said rotary part to a surface of said static part, and wherein said annular chamber extends axially from said first ring seal to said second ring seal.

9. The apparatus of claim 1, further comprising a fill-level sensor disposed to measure a liquid level in said buffer chamber.

10. The apparatus of claim 1, further comprising an annular chamber disposed relative to said buffer chamber to enable said annular chamber to receive liquid sterilization medium from said buffer chamber.

11. The apparatus of claim 1, further comprising a heater in said buffer chamber for promoting excitation of said liquid sterilization medium within said buffer chamber, said excitation being selected to result in promoting separation of bactericidal constituents from said liquid sterilization medium.

12. The apparatus of claim 1, further comprising a rotor having treatment positions on a periphery thereof, said rotor being driven to rotate about a machine axis, each of said treatment positions comprising a treatment head, wherein said treatment head is configured to switch between delivering a sterile medium and delivering a sterile medium that has been mixed with an atomized spray of liquid sterilization medium.

13. A process for using a product that comprises an apparatus for use in container treatment, said apparatus comprising a rotary feed for supplying first and second media from a stationary reference frame to nozzles being moved by a rotor around an axis of rotation, said rotary feed comprising a static part, a rotating part, and a buffer chamber, wherein, during operation, said rotating part rotates with said rotor, said static part remains stationary relative to said stationary reference frame, and a barrier medium charges said buffer chamber at a transition between said static and rotating parts, wherein said static part and said rotating part run adjacent to one another, wherein said static part and said rotating part define a flow channel for a first medium, wherein said flow channel is sealed, wherein said buffer chamber at least partially surrounds said static and rotating parts, wherein said buffer chamber surrounds said transition between said static and rotating parts, and wherein an outlet connects said buffer chamber to a treatment head to permit a medium in said buffer to be fed to said nozzle for container treatment, wherein said process comprises delivering media to said treatment head for treating containers, wherein delivering media comprises placing a container into a treatment station on a periphery of said rotor, which rotates relative to a stationary reference frame, passing said first medium into said rotary feed that comprises said rotating part that moves with said rotor and said static part that remains stationary relative to said stationary reference frame, passing a second medium into said rotary feed, and conveying said first medium to said treatment head, and conveying said second medium to said treatment head, wherein passing a first medium comprises passing said first medium into said flow channel, which is formed by said static and rotating parts, and wherein passing said second medium comprises passing said second medium into buffer chamber, which at least partially surrounds said static part and said rotating part.

* * * * *